Figure 9:
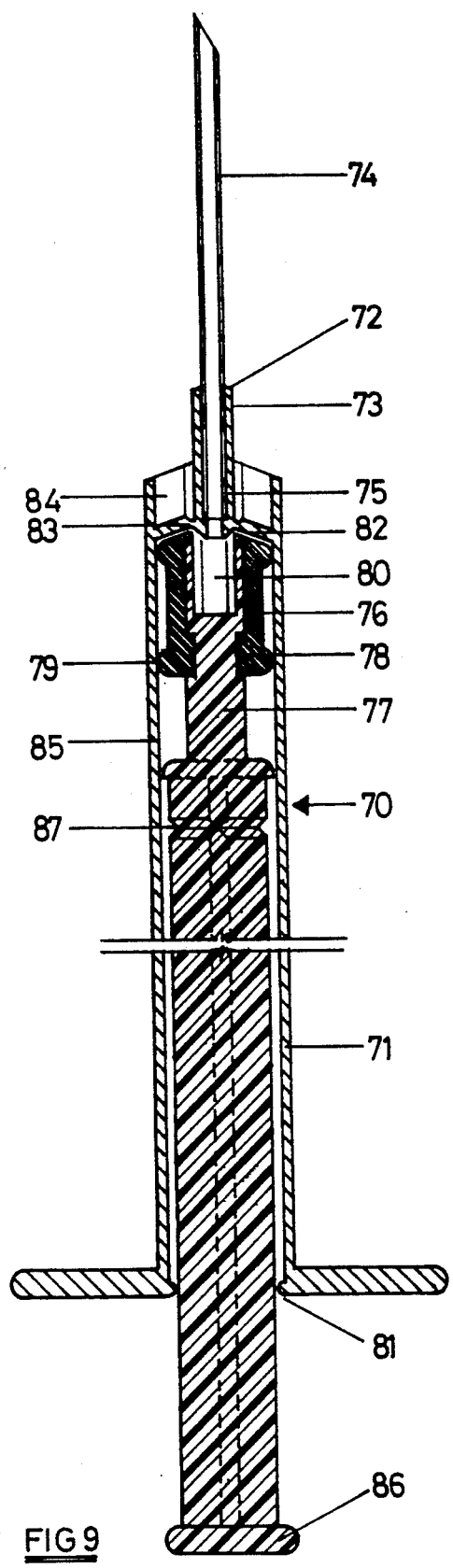

United States Patent [19]

Williams

[11] Patent Number: 5,318,536
[45] Date of Patent: Jun. 7, 1994

[54] DISPOSABLE HYPODERMIC SYRINGE WITH RETRACTABLE NEEDLE

[76] Inventor: Graham H. Williams, 18 Maple Road, Surbiton, Surrey KT6 4AB, England

[21] Appl. No.: 807,842
[22] PCT Filed: Jul. 10, 1990
[86] PCT No.: PCT/GB90/01063
  § 371 Date: Jan. 10, 1992
  § 102(e) Date: Jan. 10, 1992
[87] PCT Pub. No.: WO91/00750
  PCT Pub. Date: Jan. 24, 1991

[30] Foreign Application Priority Data

Jul. 11, 1989 [GB] United Kingdom ............ 8915919
Jan. 9, 1990 [GB] United Kingdom ............ 9000487
Jun. 21, 1990 [GB] United Kingdom ............ 9013883

[51] Int. Cl.5 .................................... A61M 5/00
[52] U.S. Cl. ............................ 604/110; 604/195
[58] Field of Search ............. 604/195, 110, 187, 218

[56] References Cited

U.S. PATENT DOCUMENTS

| 4,026,287 | 5/1977 | Haller | 604/195 |
| 4,507,117 | 6/1989 | Vining et al. | 604/196 |
| 4,692,156 | 9/1989 | Haller | 604/195 |
| 4,710,170 | 12/1987 | Haber et al. | |
| 4,747,830 | 5/1988 | Gloyer et al. | |
| 4,767,413 | 8/1988 | Haber et al. | 604/198 |
| 4,838,870 | 6/1989 | Haber et al. | |
| 5,000,738 | 3/1991 | LaVallo et al. | 604/195 |
| 5,053,010 | 10/1991 | McGary et al. | 604/110 |

FOREIGN PATENT DOCUMENTS

| 0282097 | 9/1988 | European Pat. Off. |
| 0288003 | 10/1988 | European Pat. Off. |
| 0327061 | 8/1989 | European Pat. Off. |
| 0360313 | 3/1990 | European Pat. Off. |
| 0364387 | 4/1990 | European Pat. Off. |
| 0388137 | 9/1990 | European Pat. Off. |
| 0402908 | 12/1990 | European Pat. Off. |
| 89/00435 | 1/1989 | PCT Int'l Appl. |
| 8909075 | 10/1989 | World Int. Prop. O. |

Primary Examiner—John D. Yasko
Attorney, Agent, or Firm—Ladas & Parry

[57] ABSTRACT

A disposable hypodermic syringe is disclosed having a barrel (4), a hub (1) and needle holder (2) locatable on the barrel, a plunger (5) with a piston (13) at one end thereof slideable within the barrel, and an interlockable structure on the plunger and needle holder for interlocking the same one relative to the other so that after use the needle (3) is fully retractable into the syringe barrel (4) to prevent accidental stabbing and risk of infection. The needle holder tube (2) has internal barbs (10) which engage behind a domed head (8) of the plunger (5). During use (suction and injection delivery) the plunger domed head (8) is retained behind a membrane (14) within the piston (13) by similar internal barbs (20) inside the piston (13). Preferably the interconnection between the needle holder (2) and hub (1) is a screw thread and the plunger is rotatable to detach the needle holder (2) and needle from the hub. In one alternative form the needle (3) is supported in the needle holder (2) by a weakened structure breakable by axially applied pressure upon the piston rod (5). The weakened structure (44) is generally of a thinner molded thickness than the remaining molding and is further weakened by Gamma Irradiation or other electron beam.

14 Claims, 5 Drawing Sheets

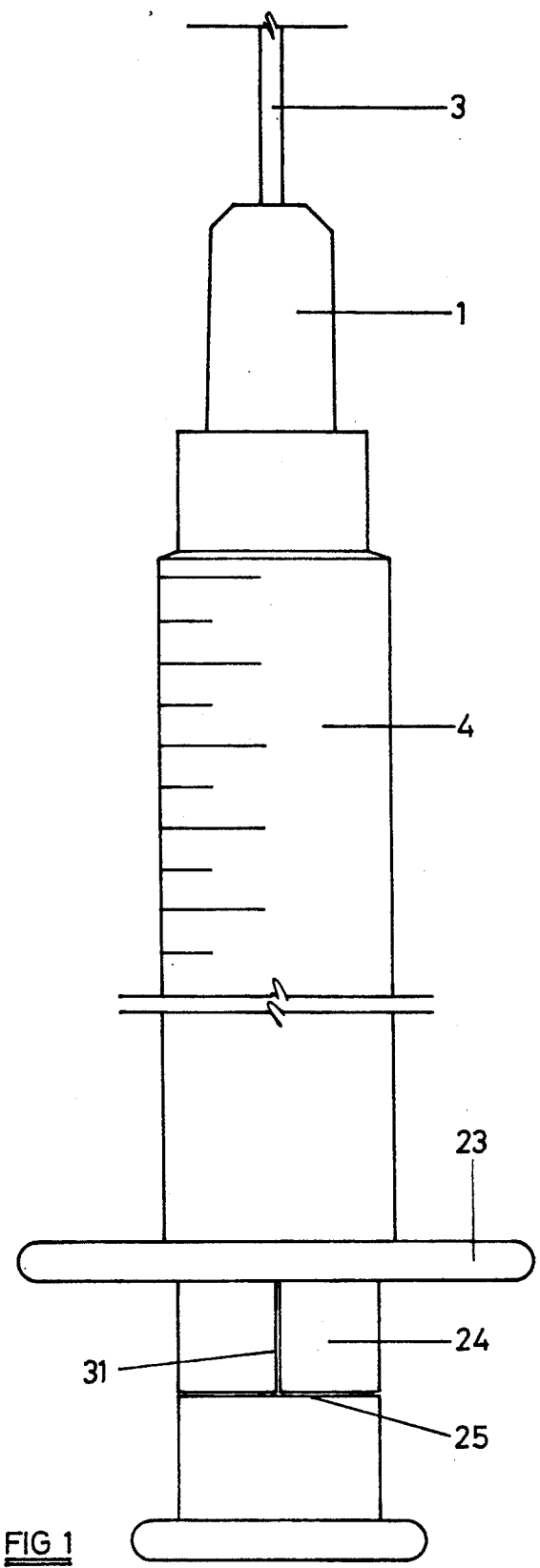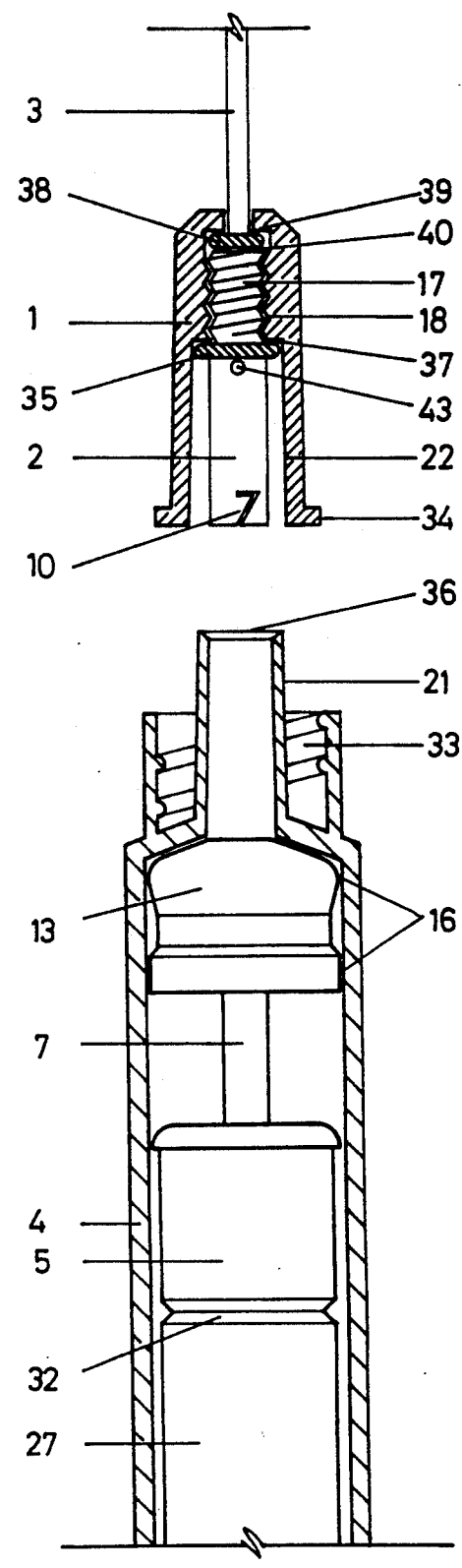
FIG 1
FIG 2

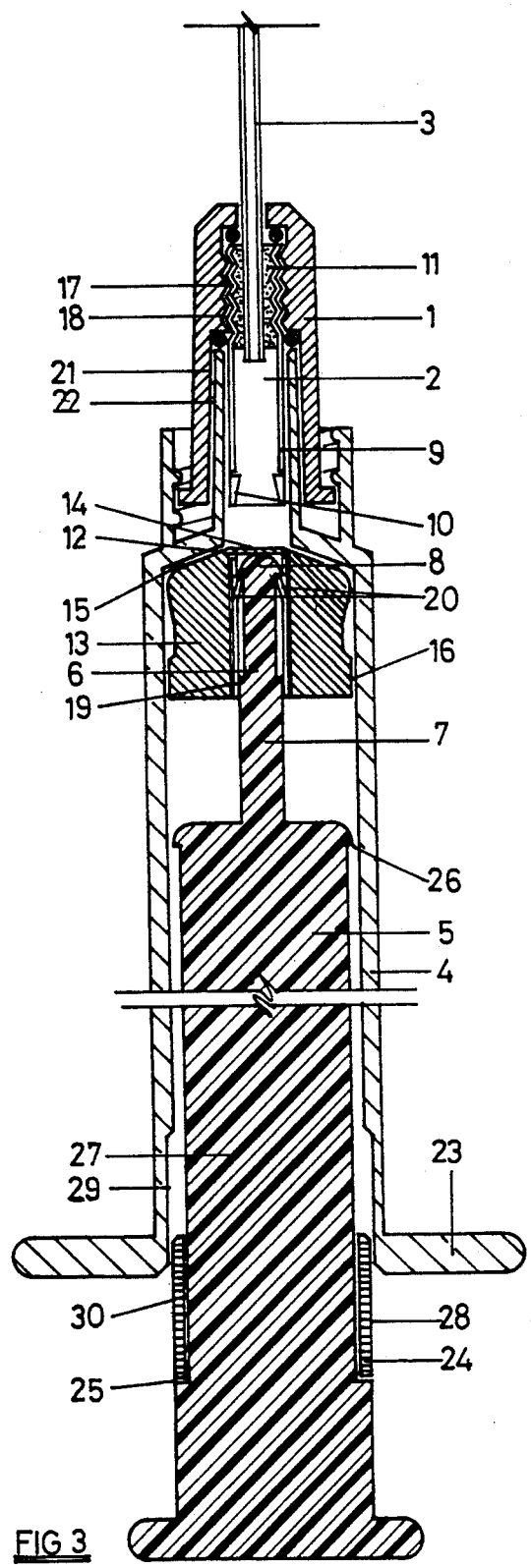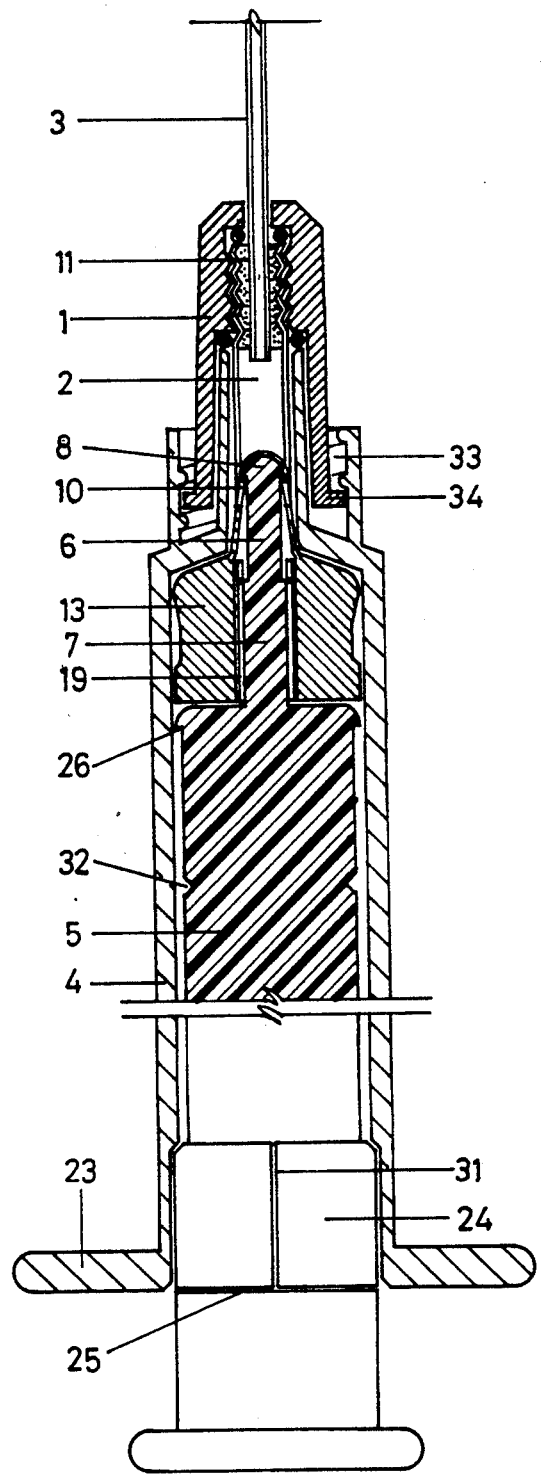
FIG 3
FIG 4

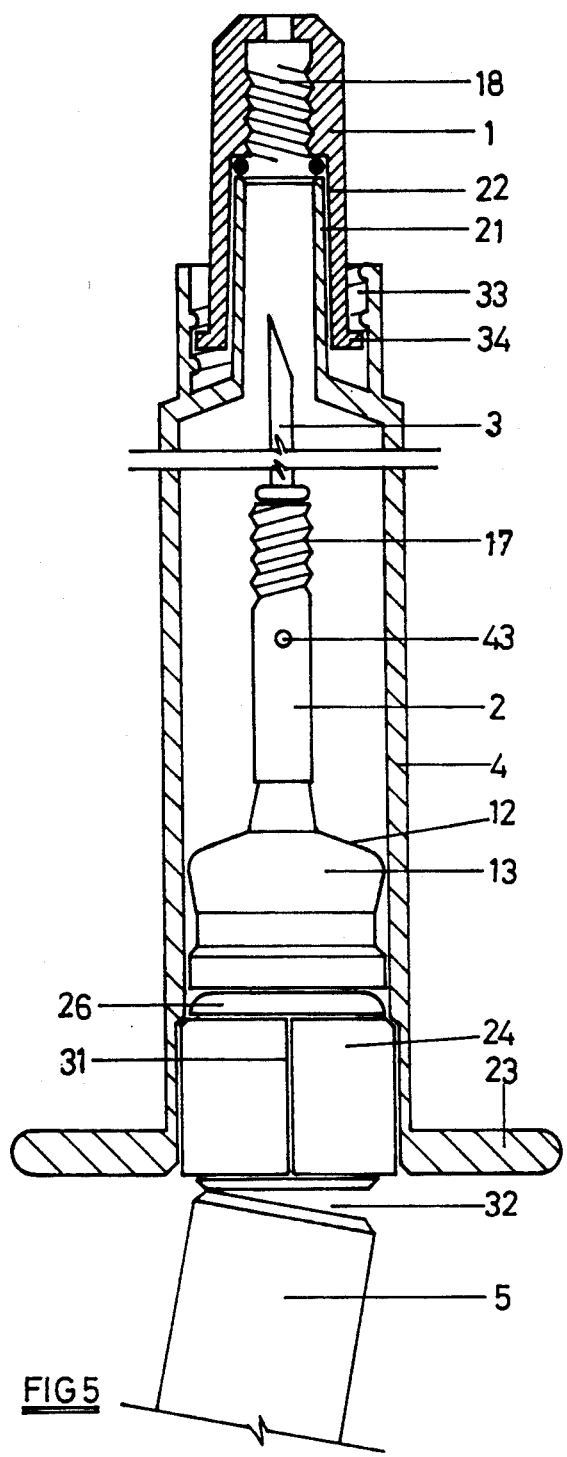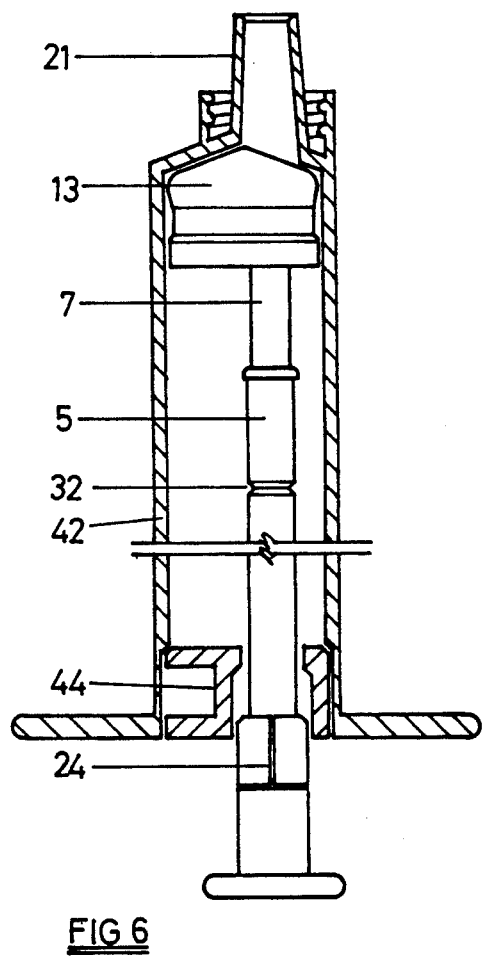
FIG 5
FIG 6

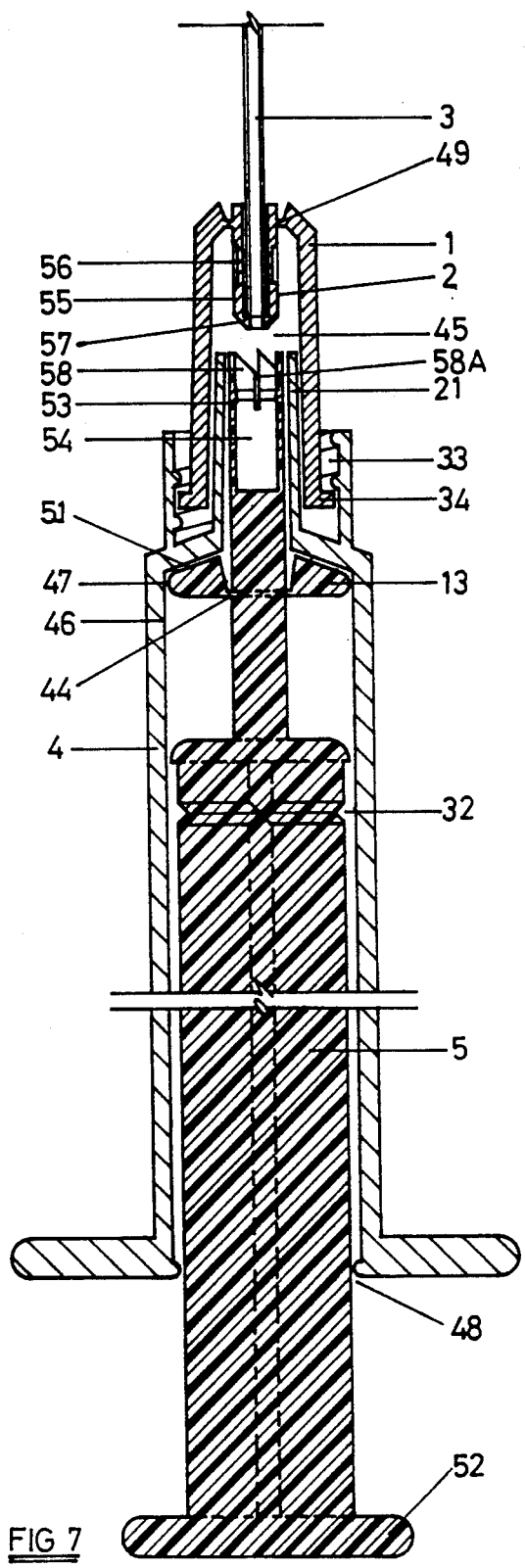
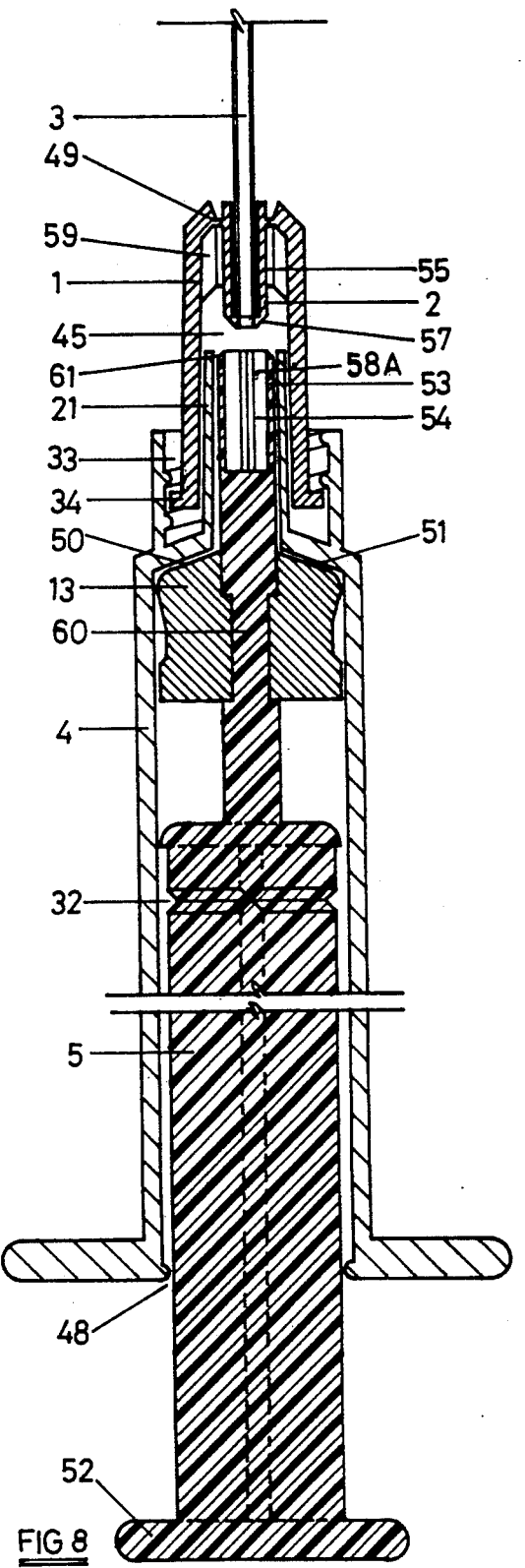
FIG 7
FIG 8

DISPOSABLE HYPODERMIC SYRINGE WITH RETRACTABLE NEEDLE

This invention relates to a disposable hypodermic syringe wherein after use the needle can be fully retracted into the barrel to prevent accidental stabbing, and consequential risk of infection from contaminated needles, which has now become an even more important issue, with the advent of communicable diseases such as AIDS and Hepatitis.

An object of the present invention is to provide a fool-proof disposable hypodermic syringe in which a needle is conveniently and completely retracted (after use) into the syringe barrel safely out of harms way, without a significant increase in the cost of the manufacture of the syringe.

Many attempts have been made to improve syringes for these reasons and a number of disposable hypodermic syringes with retractable needles are known.

In particular, reference is made to U.S. Pat. No 4790822 in which the barrel or body of the syringe receives a needle holder therein with a needle fixed thereon. The holder is positioned within the barrel to enable the needle to extend therefrom for injection purposes or to retract within the barrel. The needle is loaded from the opposite end of the body to that from which the needle projects in use. U.S. Pat. Nos. 4,767,413 and 4,258,713 as well as International published application No WO 89/00435 disclose the use of an axial compression spring located in the barrel surrounding the needle to retract the needle into the respective barrel upon completion of an injection. U.S. Pat. No. 4,790,827 discloses a vacuum tube phlebotomy (instead of a piston and plunger) with the tube slidable in a barrel carrying the needle as well as an outer shield slidable on the barrel protecting the needle rather than a retractable needle. Finally, U.S. Pat. No. 4,692,156 to Haller shows a syringe barrel having a bore at one end for supporting a needle and needle holder introduced into the barrel through the end opposite to that having the bore and a seal bonded to the needle which is sufficiently resilient to pull through the bore when a piston rod engages the innermost end of the needle and allow retraction of the whole needle into the syringe.

However, none of these devices provide a relatively simple, cheap, efficiently operable syringe barrel to which is attachable any one of a number of separate needles of various sizes.

According to the invention there is provided a disposable hypodermic syringe comprising a syringe body, a separately attachable hub mountable upon the body at one end thereof, and a piston means mountable in the body and being slidable along the body from a distal end thereof remote from the said one end, the hub including a needle holder arranged to support a hypodermic needle therein, characterised in that the needle holder is attached to the hub by frangible means so that the piston means interengages with the needle holder when the piston means is substantially fully displaced toward the needle holder, whereby in response to retraction of the piston means the frangible means is broken, the needle holder is disengageable from the hub, and the needle holder and needle are completely withdrawn into the syringe.

Preferably, the needle means comprises a support member and a needle mounted on the support member. Moreover, the piston means may comprise a piston and a piston rod. Conveniently, when the needle and needle holder are to be retracted into the syringe the piston rod is movable relative to the piston, the engagable means being located on the piston rod.

Preferably, the frangible means comprises weakened integral moulding. Conveniently, the weakened integral moulding is enhanced by Gamma Irradiation or any other electron beam radiation sterilisation process.

Embodiments of a syringe will now be described by way of example with reference to the accompanying drawings in which:

FIG. 1 is an external view of an assembled syringe.

Figure 10:
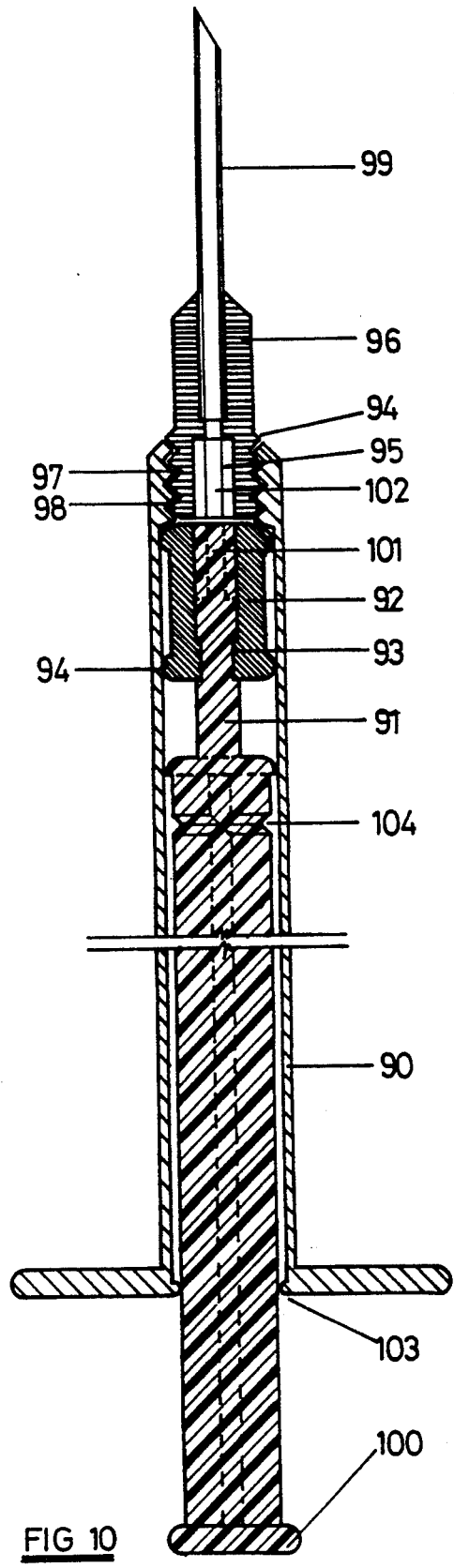

FIG. 2 is an internal part sectional view of a syringe barrel sub-assembly and needle holder sub-assembly of the syringe of FIG. 1 prior to assembly, FIG. 3 is a sectional view of the assembled syringe of FIG. 1, FIG. 4 is a sectional view of the syringe of FIG. 1 showing a domed head of the plunger, fully engaged and entrapped in needle holder barbs prior to unscrewing and retraction of the needle, FIG. 5 is a sectional view of the syringe of FIG. 1 showing needle holder fully retracted and plunger shaft broken off at a weak section, FIG. 6 is a sectional view of a syringe having an eccentric barrel but embodying the plunger and needle holder construction of the syringe of FIG. 1, FIG. 7 is a longitudinal sectional view of an embodiment of a syringe according to the present invention, FIG. 8 is a longitudinal sectional view of a modified form of the embodiment of FIG. 7, FIG. 9 is a longitudinal sectional view of another embodiment of a syringe according to the present invention, and FIG. 10 is a longitudinal sectional view of a syringe having a friction fit between piston and needle holder.

Referring to the drawings FIGS. 1 to 6 disclose a disposable hypodermic syringe comprising a separate attachable hub 1 in which is locatable a concentric needle holder 2 with an internal integral hypodermic needle 3. The holder 2 is separable from the hub 1 and fully retractable (after use) into a barrel 4.

A piston rod 5 is slidably located within the syringe barrel 4. The piston rod 5 has a shaft 7 terminating at its innermost end within the syringe with an integral domed shaped head 8 adjacent to which is fluting 6. The needle holder 2 includes a hollow tube 9 having a matching internal diameter with the domed head 8 of the piston rod 5 and provided with internal integral sprung barbs 10 formed out of the wall of the tube 9 to enable entry of the domed head 8 until the barbs 10 spring back internally onto the fluted neck 6 behind domed head 8 to entrap the domed head.

The needle 3 and the needle holder tube 9 are integrally joined by an inert jointing medium 11 and/or integral inert plastic moulding 11. To prevent premature retraction (of the needle 3 and needle holder 2) into the barrel 4, the domed head 8 of the piston rod 5 is retained behind the piston face 12 and within the piston 13 by a rubber (or synthetic rubber) membrane 14 so provided to form the piston head 12 or pressure face 12 of the piston 13. The membrane 14 preferably comprises an integral moulding 15 with the piston 13 and/or piston sealing rings 16 but may be omitted.

The separable engagement between needle holder tube 9 and hub 1 comprises an external screw thread 17 on the needle holder tube 9 and a matching internal thread 18 on the corresponding mating section of the hub 1.

The hub 1 is manufactured from an inert material preferably plastics and the thread form and tolerances of the mating threads 17 and 18, embody an airtight and/or a liquid tight seal, and are also unscrewable by twisting the piston rod 5 after it is entrapped by the barbs 10 acting against the flutes 6 of the neck 7 of piston rod. Reference herein to an airtight seal is to be taken as including a liquid tight seal. To facilitate withdrawal of the piston 13 during a suction stroke the piston has located therein an internal concentric tube 19 having internal integral sprung barbs 20 formed out of the wall of the tube 19 to enable entry of piston rod darned head 8 (during assembly) into the piston 13 until the piston tube barbs 20 spring inwardly behind the domed head 8 on to the neck 7 of the piston rod 5 to entrap the domed head 8 (thus facilitating withdrawal of the piston during the suction stroke of the syringe).

The length of the neck section 7 of the piston rod 5 is such as to permit sufficient forward movement of the piston rod 5 to enable penetration beyond the piston face 12 and into the needle holder tube barbs 10 (when said needle engagement/retraction is required).

The hub 1 is attached to syringe barrel 4 by the provision of a concentric mating tapered male nozzle 21 on syringe barrel 4 and the provision of a matching air tight and/or liquid tight internal taper seal 22 within hub 1.

The gradient of the taper 22 used is 6% and/or any standard taper to conform with the accepted medical standards prevailing.

Finger grips 23 are provided on the syringe barrel 4 at the piston rod 5 operating end of the barrel 4.

A concentric bush or collar 24 is provided inside the barrel 4 at the finger grip end together with integral matching shoulder stops 25 and 26 at suitable locations On both ends of the piston rod 27 to act as stops to prevent premature penetration of the piston head membrance 14 and also to prevent premature dismantling of the syringe assembly during the suction stroke respectively.

The dimensional tolerances of the bush 24 are such that its outside diameter 28 is an interference (but movable) fit with the internal bore 29 of the barrel 4 and also the inside diameter 30 of the bush 24 is an easy slide fit with the piston rod 27. The bush 24 is provided with a circumferencial split 31 to enhance feasibility of this construction.

A weak spot or weak section 32 is provided on an appropriate location of the plunger rod 27 to enable it to be broken off when the needle holder 2 and needle 3 have been fully retracted (after use) into the barrel 4.

The hub 1 and syringe barrel 4 are additionally provided with mating thread fittings 33 and 34 to reinforce the airtight and/or liquid tight seal between the taper 22 and nozzle 21 fitting.

The mating screw fittings 33 and 34 conveniently conform, with British Standard 3930 cart 2, and/or any accepted medical standards prevailing.

Sealing between needle holder tube 2 and barrel 4 is reinforced by an O-ring seal 35 located around the needle holder tube 2 and between the end face 36 of the syringe barrel nozzle 21 and the internal face 37 of the hub 1 to act as an additional liquid and/or airtight seal.

An additional O-ring seal 38 is located around the needle 3 between the end face 40 of the needle holder 2 and the mating internal face 39 of the hub 1 to serve as an additional liquid tight and/or airtight seal.

Conveniently the needle holder tube 2 is provided with at least one hole 43 to facilitate the release of trapped air when the syringe is being primed prior to injection.

In one alternative embodiment as shown in FIG. 6 the axis of the barrel 4 and piston 13 are eccentric one relative to the other but parallel to the common axes of all the other working components of the syringe which are otherwise of an identical construction to that described above in relation to FIGS. 1 to 3.

A guide 41 is provided at the finger grip end of the eccentric barrel 42 to ensure adequate alignment of axes of all the other working components.

The eccentric construction conforms to BS 5081 part 1, and/or any accepted medical standards prevailing.

FIG. 7 illustrates one form of a syringe according to the invention comprising a tubular barrel 4 having a nozzle 21 formed at one end 45 and a piston 13 attached to a piston rod 5 by a continuous integral breakable moulding 44. The moulding 44 forms an air/liquid tight seal in normal use between the piston and piston rod. A further seal is provided between the internal wall 46 of the barrel and piston at 47. The piston and piston rod are slideable along and within the barrel from distal end 48 thereof remote from the one end 45. An attachable needle assembly comprising a separate hub 1 is mountable upon the nozzle 21, such mounting being reinforced by the provision of an interengagable thread fitting 33, 34 integral with the one end of the barrel, The hub 1 includes a needle holder 2 releasably attached to and about the central axis of the hub 1 by a continuous integral frangible moulding 49, which needle holder is arranged to support a hypodermic needle 3 therein, the needle holder and needle being retractable (after use) into the syringe barrel.

Retraction of the needle and needle holder is achieved, after use, and when the front face 50 of the piston 13 is adjacent to and touching the internal end wall 51 of the barrel 4, by applying pressure to a thumb push 52 at the rearward end of the piston rod 5. Such pressure is sufficient to break the moulding 44 between piston 13 and piston rod 5 to allow the piston rod to slide for-ward within the piston, along the axis of the barrel, and to protrude from the mouth of the nozzle 21 and engage needle holder 2.

Interengagement between the needle holder and piston rod is facilitated by a female engagement device 53 comprising a fluted and/or shouldered recess 54 provided at the forward end of the piston rod 5. A male mating engagement device 55 comprising a fluted and-/or necked shaft 56 terminating with a domed and/or tapered head 57 is provided on the needle holder 2. The needle holder has a matching external diameter with fluted and/or shouldered recess 54, tapered head 57 promoting ingress to recess 54 until the neck of shaft 56 locates behind the shoulders of the recess 54 and is so entrapped within the recess. Such location prevents the piston rod from being retracted prior to disengagement of needle older from the hub.

To facilitate disengagement of needle holder 2 from hub 1 a continuous breakable moulding 49 is provided between the needle holder and the hub. Disengagement is achieved by applying pressure to the external end of the piston rod and twisting of an integral angled moulding 58 (formed at the mouth of the female engagement device 53) against the breakable moulding 49 until the moulding breaks and disengages the entrapped needle holder 2 from the hub 1.

When disengagement of needle holder and hub has been accomplished, the entrapped needle holder 2 and its supported hypodermic needle 3 are retracted into the barrel 4 by the action of the suction stroke of the piston rod 5. The hub 1 remains attached to the nozzle 21 by thread fitting 34.

Disengagement of piston rod 5 from piston 13 is achieved at breakable moulding 44 and disengagement of needle holder 2 from hub 1 at breakable moulding 49. The complete syringe and needle assemblies are manufactured of materials that may be subjected to sterilisation methods such as Gamma Irradiation or other electron beam radiation/sterilisation process to an intensity that provides an acceptable level of sterilisation whilst for the most part retaining the structural integrity of the materials but rendering the frangible mouldings 44 and 49 (because of their moulded configuration) structurally weaker and susceptible to breakage under the pressures and twisting required in the physical actions of disengagement as just described herein.

FIG. 8 shows a modified form of the syringe of FIG. 7 in which a piston 13 is substantially larger than the piston 2 of FIG. 7 and is separately mountable on the piston rod and held in position thereon by recessess 60 in the piston rod. The bore of the piston through which the piston rod passes is of a corresponding shape to the shape of the piston rod to prevent movement of the piston along the rod during normal use of the syringe.

However, when liquid within the syringe is dispelled by moving the piston rod towards the needle the forward face of the piston engages the end of the syringe barrel which acts as a stop. The piston which is preferably of a resilient rubber material has sufficient resilience to allow the piston rod to pass therethrough upon the application of further pressure to engage the end of the piston rod with the needle holder and to break the frangible integral moulding 49 supporting the needle holder. The needle holder 2 is further supported in FIG. 8 by frangible mouldings 59 extending radially from the needle holder to the hub 1.

In this embodiment the recessed end of the piston rod has a tapered edge 61 to cut the frangible integral moulding 49, 59 supporting the needle holder to release the holder. Moreover, the internal diameter of the recess is without projections or shoulders 53 and is of such a diameter as to be an interference fit with axially extending outer contact surfaces of the needle holder 2. The interference fit is sufficiently strong to facilitate withdrawal of the needle holder into the syringe barrel after the integral support moulding is broken. Such an interference fit may be used in the embodiment to FIG. 7 thereby omitting the serrations 58 and shoulders 53 of the piston rod recess diametrically opposed axially extending slots 58A are defined in the piston rod in the wall of the recess 54.

Preferably, the needle holder of either of the FIG. 7 or FIG. 8 embodiments may be supported by additional frangible radially extending mouldings 59 located between the needle holder and hub.

Referring to FIG. 9 there is shown a disposable needle retracting hypodermic syringe 70 comprising a tubular barrel 71 formed at one end 72 with a releaseable attached needle holder 73 which supports a hypodermic needle 74 and which is provided with an elongate body 75 through which the needle 74 passes. A piston 76 is realeaseably attached around a piston rod 77 with piston 76 and piston rod 77 having an air/liquid tight seal therebetween at 78 and between the internal wall of the barrel at 79. The piston 76 is otherwise fixed relative to the piston rod 77, during normal use of the syringe, by a similar arrangement to that described with reference to the embodiment of the grate.

The piston rod 77 is also provided with a central axially extending recess 80 corresponding in internal diameter to the external diameter of the body 75 of the needle holder. The piston and piston rod are slidable along the barrel from distal end 31 thereof remote from the one end 72. The needle holder is joined to the one end of the barrel and to the barrel end wall 82 by integral moulding 83 provided with a frangible section or sections. The integral moulding is reinforced by frangible radial vanes 84 between the needle holder and barrel wall 85.

When an injection is completed or the needle holder is otherwise required to be retracted into the syringe body additional pressure is applied to piston rod thumb push 86 to facilitate engagement of piston rod 77 with the needle holder 73. The additional pressure is sufficient for the piston rod 77 to detach itself from and slide forward towards the needle holder within piston 76. The forward end of the piston rod or open end of the recess 80 engages the frangible connection 83 and breaks that connection. As the piston rod continues to move forward the open end of the recess 80 breaks the frangible interconnection of the radial vanes 84 with the wall 75 of the needle holder 73. Whilst this breakage of the frangible connections is achieved the end of the piston rod surrounds the needle holder and attaches itself to the needle holder by virtue of the interference fill therebetween. The detached needle holder and its supported hypodermic needle are then fully retracted into the syringe barrel 71 by pulling the piston rod out of the syringe barrel at the distal end 81 until a weakened portion 87 of the piston rod 77 is exposed outside the needle barrel whereupon pressure applied laterally to the links of the piston rod causes the piston rod to break off at 87.

As with the previous embodiments which have been described with frangible connections supporting the needle holder, the weakening of the frangible integral support mouldings for the needle holder is enhanced by subjecting the syringe and needle holder to Gamma Irradiation or other electron beam, sterilisation processes because of the molecular change in the plastics material from which the syringes are manufactured. Therefore, whilst an acceptable level of sterilisation is achieved the integral frangible wall and vanes are structurally weakened and more susceptible to breakage under the pressures applied.

Referring now to the FIG. 10 there is shown a further syringe 90 having a piston rod 91 on which is mounted piston 92 fixed relative to the piston rod 91 in the same manner as described with reference to FIG. 8 by the provision of recesses 93 in the piston rod. The piston 92 is sealed relative to the piston rod 91 along the contact surface in the recess 93 and also to the syringe barrel at the point 94. However, in this instance the end of the piston rod is not recessed but is provided with an engagement device for engagement with a recess 95 in needle holder 96 which is adapted to be directly mounted on the body of the syringe barrel by a coarse screw thread arrangement 97, 98. The coarseness of the thread is such as to allow the needle holder to be inserted or released from the syringe barrel by rotating the needle holder trough less than 360° in its preferred form. Degress of rotation of more than 360° may be usable. A needle 99 is supported in the needle holder 96 by a jointing medium which in itself is well known.

When an injection is completed or the needle holder is otherwise required to be retracted into the syringe body additional pressure is applied to piston rod thumb push 100 to facilitate engagement of piston rod 91 with needle holder 96 by the insertion of the end of the piston rod 91 into the recess 95 within the needle holder 96 to thereby engage cooperative engagement devices 101, 102 on the end of the piston rod and in the recess respectively. Once the engagement devices have interlocked the piston rod is rotated and the screw thread forces the needle holder into the syringe barrel whereby upon release from the screw thread the piston rod 91 is pulled out from the syringe barrel 90 at distal end 103 until a weakened area 104 on the piston rod is exposed externally of the syringe barrel at distal end 103. At this point, the needle holder 96 and needle 99 are fully retracted into the syringe barrel 90. Lateral pressure is then applied to the length of the piston rod and the piston rod breaks at the weakened area 104 thereby entrapping the needle and needle holder within the syringe barrel.

The coarse screw thread 97, 98 of this syringe is an interference fit to ensure a positive air/liquid seal between the needle holder and syringe body 90.

Whilst the frangible interconnections of the various embodiments disclose herein have been broken by the piston rod prior to engagement thereof with and retraction of the needle holder, it is possible for the interengagement of the piston rod and needle holder to be such as to engaged without breaking the frangible connections, such break being effected by pulling the piston rod outwardly from the syringe barrel.

It will be appreciated that the invention is not limited to the above described and illustrated embodiments, that other modifications and embodiments of the present invention will be apparent to the skilled reader, and that all such modifications and embodiments are to be deemed to be within the scope of the present invention.

I claim:

1. A disposable hypodermic syringe comprising a syringe body having a fixed end wall with an aperture therein through which fluid is passed from the syringe, a separately attachable hub mountable upon the fixed end wall at one end of the syringe, and piston means mountable in the syringe body and being slidable along the body from a distal end thereof remote from the said one end, the piston means comprising a piston and a piston rod which are movable one relative to the other, the piston rod having a recess extending axially along the piston rod from the one end thereof and a shoulder extending inwardly from the inner wall of the recess, the hub including a needle holder supporting a hypodermic needle therein and mounted on the hub by frangible means so that the piston rod interengages with the needle holder when the piston rod is substantially fully displaced toward the needle holder and extends through the aperture in the end wall of the syringe body, whereby in response to pressure on the frangible means the frangible means is broken to disengage the needle holder from the hub, the needle holder is held in the axial recess in the piston rod, and the needle holder and needle are completely withdrawable into the syringe.

2. A syringe as claimed in claim 1 wherein in that the frangible means comprises a weakened integral moulding between the needle holder and a hub supporting the needle holder.

3. A syringe as claimed in claim 1, including in a shoulder extends inwardly from the inner wall of the recess in the piston rod.

4. A syringe as claimed in claim 3, wherein in that the outer wall of the needle hold is fluted, each flute being arranged to receive an inwardly directed shoulder of the recess to interlock therewith for retracting the needle holder into the syringe body.

5. A syringe as claimed in claim 3 wherein in that the open end of the recess is serrated for engaging and breaking an integral web between the hub and needle holder.

6. A syringe as claimed in claim 3 wherein the open end of the recess is tapered for engaging and breaking the integral web between the hub and needle holder.

7. A syringe as claimed in claim 6, characterised in that the wall of the recess includes diametrically opposed axially extending slits therein extending from the said one end of the piston rod.

8. A syringe as claimed in claim 6, including in a shoulder extending inwardly from the inner wall of the recess in the piston rod, said shoulder constituting part of the interengagement means between the piston rod and needle holder.

9. A syringe as claimed in claim 8, wherein the outer wall of the needle holder is fluted, each flute being arranged to receive an inwardly directed shoulder of the recess to interlock therewith for retracting the needle holder into the syringe barrel.

10. A syringe as claim 1 characterised in that the inter connection between the piston rod and needle holder is such that the piston comprises a male connection and the needle holder comprises a female connection.

11. A disposable hypodermic syringe comprising a syringe body having a fixed end wall with an aperture therein.through which fluid is passed from the syringe, a separately attachable hub mountable upon the fixed end wall at one end of the syringe, and piston means mountable in the body and being slidable along the body from a distal end thereof remote from the said one end, the hub including a needle holder mounted on the hub to support a hypodermic needle therein, wherein the needle holder is attached to the hub by frangible means so that the piston means interengages with the needle holder when the piston means is substantially fully displaced toward the needle holder and extends through the aperture in the end wall, wherein the piston has a recess extending axially along the piston from the end thereof engageable with the needle holder, the outer wall of the needle holder is fluted, each flute being arranged to receive an inwardly directed shoulder of the recess to interlock therewith for retracting the needle holder into the syringe body, whereby in response to pressure on the frangible means the frangible means is broken, the needle holder id disengageable from the hub, and the needle holder and needle are completely withdrawable into the syringe.

12. A disposable hypodermic syringe comprising a syringe body having a fixed end wall with an aperture therein through which fluid is passed from the syringe, a separately attachable hub mountable upon the fixed end wall at one end of the syringe, and piston means mountable in the body and being slidable along the body from a distal end thereof remote from the said one end, the hub including a needle holder mounted on the hub to support a hypodermic needle therein, wherein the needle holder is attached to the hub by frangible means so that the piston means interengages with the needle holder when the piston means is substantially fully displaced toward the needle holder and extends through the aperture in the end wall, wherein the piston has a recess extending axially along the piston from the end thereof engageable with the needle holder, the outer wall of the needle holder and one end of the piston rod include interlocking means to interlock one with the other for retracting the needle holder into the syringe body, whereby in response to pressure on the frangible means the frangible means is broken to disengage the needle holder from the hub, the needle holder is held in the axial recess in the piston rod and the needle holder and needle are completely withdrawable into the syringe body.

13. A syringe as claimed in claim 12, wherein the wall of the recess includes diametrically opposed axially extending slits therein extending from the said one end of the piston rod.

14. A syringe as claimed in claim 12, wherein the interlocking means comprises an interference fit between the outer surface of the needle holder and the inner surface of the recess in the one end of the piston rod.

* * * * *